(12) United States Patent
Drake, Jr.

(10) Patent No.: US 7,286,241 B2
(45) Date of Patent: Oct. 23, 2007

(54) SYSTEM AND METHOD FOR HIGH-SPEED LASER DETECTION OF ULTRASOUND

(75) Inventor: Thomas E. Drake, Jr., Ft. Worth, TX (US)

(73) Assignee: Lockheed Martin Corporation, Bethesda, MD (US)

( * ) Notice: Subject to any disclaimer, the term of this patent is extended or adjusted under 35 U.S.C. 154(b) by 305 days.

(21) Appl. No.: 10/152,743

(22) Filed: May 22, 2002

(65) Prior Publication Data

US 2002/0186380 A1 Dec. 12, 2002

Related U.S. Application Data

(63) Continuation-in-part of application No. 09/344,298, filed on Jun. 24, 1999, now Pat. No. 6,483,859.

(51) Int. Cl.
*G01B 9/02* (2006.01)

(52) U.S. Cl. ........................................ 356/502; 356/432
(58) Field of Classification Search ................ 356/502, 356/432, 237
See application file for complete search history.

(56) References Cited

U.S. PATENT DOCUMENTS

| | | | |
|---|---|---|---|
| 3,911,733 A | 10/1975 | Bhuta et al. | 73/88 |
| 3,992,627 A | 11/1976 | Stewart | 250/312 |
| 4,046,477 A | 9/1977 | Kaule | 356/109 |
| 4,121,470 A | 10/1978 | Kaule | 73/643 |
| 4,349,112 A | 9/1982 | Wilks et al. | 209/538 |
| 4,355,538 A | 10/1982 | Hall | 73/811 |
| 4,422,177 A | 12/1983 | Mastronardi et al. | 378/17 |
| 4,553,238 A | 11/1985 | Shaw et al. | 372/6 |
| 4,713,822 A | 12/1987 | Lee | 372/69 |
| 4,803,639 A | 2/1989 | Steele et al. | 364/507 |

(Continued)

FOREIGN PATENT DOCUMENTS

| | | |
|---|---|---|
| EP | 0103382 A2 | 5/1985 |
| EP | 0136871 A2 | 11/1985 |
| EP | 0657070 A1 | 12/1994 |
| EP | 0821453 A2 | 7/1997 |

OTHER PUBLICATIONS

International Search Report, PCT.
C. Honninger, et al.; *Diode–Pumped Thin–Disk Yb: YAG Regenerative Amplifier*, Applied Physics B, pp. 423–426.

(Continued)

*Primary Examiner*—Hwa (Andrew) Lee
(74) *Attorney, Agent, or Firm*—Garlick, Harrison & Markison; Robert McLauchian

(57) ABSTRACT

A system and method for laser light amplification provides amplification of a laser light beam emitted from a laser light source as low-amplification seed laser light signal. The low-amplification seed laser light signal is transmitted to an amplification component. The amplification component amplifies the low-amplification seed laser light signal by stimulating emissions of the population inversion provided by a pumping diode to generate an amplified laser light signal. The system and method further directs the amplified laser light signal to an output destination. The destination may be an object undergoing laser ultrasound testing. The amplified laser light may reflect with a modulation characteristic of a sound energy wave about the object. The reflected laser light may be collected by an interferometer and used in the detection and characterization of the sound energy wave. The result of the present invention is a system and method of operation providing higher pulse rates, improved pointing stability, and optionally variable pulse rates for a variety of uses, including for non-destructive laser ultrasonic testing of materials.

20 Claims, 5 Drawing Sheets

U.S. PATENT DOCUMENTS

| | | | | |
|---|---|---|---|---|
| 4,809,308 A | 2/1989 | Adams et al. | ................ | 378/99 |
| 4,841,460 A | 6/1989 | Dewar et al. | .......... | 364/571.02 |
| 5,014,293 A | 5/1991 | Boyd et al. | .................. | 378/197 |
| 5,048,026 A | 9/1991 | Shaw et al. | ..................... | 372/6 |
| 5,065,630 A | 11/1991 | Hadcock et al. | .............. | 73/802 |
| 5,086,433 A | 2/1992 | Pochelle et al. | .............. | 372/72 |
| 5,113,079 A | 5/1992 | Matulka | ..................... | 250/550 |
| 5,119,408 A | 6/1992 | Little et al. | ..................... | 378/4 |
| 5,122,672 A | 6/1992 | Mansour | ..................... | 250/571 |
| 5,140,533 A | 8/1992 | Celette | ........................ | 364/559 |
| 5,172,388 A | 12/1992 | Long et al. | ................... | 372/70 |
| 5,271,031 A | 12/1993 | Baer | ........................... | 372/93 |
| 5,285,467 A | 2/1994 | Scheps | ........................ | 372/69 |
| 5,295,073 A | 3/1994 | Celette | ....................... | 364/424 |
| 5,319,567 A | 6/1994 | Ebenstein | .............. | 364/474.34 |
| 5,335,236 A | 8/1994 | Toeppen | ...................... | 372/25 |
| 5,384,717 A | 1/1995 | Ebenstein | ..................... | 364/560 |
| 5,442,572 A | 8/1995 | Kiridena et al. | ............ | 364/560 |
| 5,490,195 A | 2/1996 | Berkley | ........................ | 378/72 |
| 5,541,856 A | 7/1996 | Hammermeister | .......... | 364/552 |
| 5,555,298 A | 9/1996 | Jonsson | ................. | 364/424.03 |
| 5,574,226 A | 11/1996 | Reuther et al. | ............... | 73/669 |
| 5,608,166 A | 3/1997 | Monchalin et al. | ........... | 73/657 |
| 5,637,812 A | 6/1997 | Baker et al. | ............... | 73/865.6 |
| 5,790,303 A | 8/1998 | Weston et al. | .............. | 359/345 |
| 5,848,115 A | 12/1998 | Little et al. | .................... | 378/4 |
| 5,872,804 A | 2/1999 | Kan et al. | ...................... | 372/93 |
| 5,930,282 A | 7/1999 | Unternahrer et al. | ......... | 372/69 |
| 5,991,315 A | 11/1999 | Injeyan et al. | ................. | 372/11 |
| 6,023,985 A | 2/2000 | Fournier | ..................... | 73/865.6 |
| 6,047,041 A | 4/2000 | Ellinger | ........................ | 378/58 |
| 6,094,447 A | 7/2000 | Drake, Jr. | ..................... | 372/75 |
| 6,134,258 A | 10/2000 | Tulloch et al. | ................. | 372/99 |
| 6,157,663 A | 12/2000 | Wu et al. | ...................... | 372/75 |
| 6,167,181 A | 12/2000 | Fukaishi | ...................... | 385/123 |
| 6,205,240 B1 | 3/2001 | Pietrzak et al. | ............. | 382/152 |
| 6,220,099 B1 | 4/2001 | Marti et al. | ................... | 73/633 |
| 6,285,704 B1 | 9/2001 | Kullander-Sjoberg et al. | ............ | 372/96 |
| 6,360,621 B1 | 3/2002 | Eldred et al. | .............. | 73/865.6 |
| 6,378,387 B1 | 4/2002 | Froom | ........................ | 73/865.8 |
| 6,466,643 B1 | 10/2002 | Bueno et al. | .................. | 378/58 |
| 6,571,008 B1 | 5/2003 | Bandyopadhyay et al. | . | 382/154 |
| 6,637,266 B1 | 10/2003 | Froom | ........................... | 73/583 |
| 6,711,954 B2 * | 3/2004 | Drake, Jr. | ..................... | 73/655 |

OTHER PUBLICATIONS

Steven Jackel, et al.; *High–Energy Nd:Dr:GSGG Lasers Based on Phase and Polarization Conjugated Multiple–Pass Amplifiers*; Optical Engineering, vol. 36, No. 7, Jul. 1997, pp. 2031-2036.

K. F. Wall, et al.; *A Ti:Al$_2$O$_3$ Master–Oscillator/Power–Amplifer System*; IEEE Journal of Quantum Electronics, Jun. 1993, No. 6, pp. 1505–1514.

NTIAC Newsletter; vol. 27, No. 5, Sept. 2002, 5 pp.

Froom, Douglas A., et al.; Solving Problems with Advanced Technology, 1999 IEEE, 4 pp.

Alkire, M. G., Department of the Air Force Memo regarding Construction Project Data; May 7, 1982, Bates 000010 through Bates 000068.

U.S. Air Force, Military Construction Project Data, Apr. 14, 1982, Bates 000074 through Bates 000129.

U.S. Air Force, Attachment I to Request for Environmental Impact Analysis, Dec. 2, 1982, Bates 000130 through 000167.

Stanghellini, Frank D., Department of the Air Force Memo regarding Criteria Changes, Jan. 9, 1985, Bates 000168 through 000214.

Metro Today, The Sacramento Union; May 12, 1983, Bates 000215 through Bates 000216.

Letter Contract Between Department of the Air Force and Par Systems Corp. Aug. 3, 1984, Bates 000217 through Bates 000312.

Timeline and Equipment List for Contract Between Department of The Air Force and Par Systems Corp., Aug. 3, 1984, Bates 000313 through Bates 000325.

Civilian Personnel Position Description, Department of the Air Force; Jul. 10, 1989, Bates 000328 through Bates 000332.

Aviation Week & Space Technology, Mar. 13, 1989, Bates 000333 through Bates 000336.

UltraOptec, Laser Ultrasonic System, 1999 IEEE, Bates 000337 through Bates 000340.

J. W. Bader, et al., Laser Ultrasonics or Alternative NDI Composite Defect, Nov. 20, 1990, Bates 000342 through Bates 000446.

Douglas A. Froom, Statement of Work for Advanced Ultrasonic Component Inspection System, Jul. 14, 1993, Bates 000447 through 000490.

Award of Contract from Department of the Air Force, Aug. 11, 1993, Bates 000491 through Bates 000492.

UltraOptec, Luis Phase 3 Acceptance Test Report, Feb. 16, 1996, Bates 000493 through Bates 000501.

Spacemaker, Feb. 22, 1996, Bates 000502.

* cited by examiner

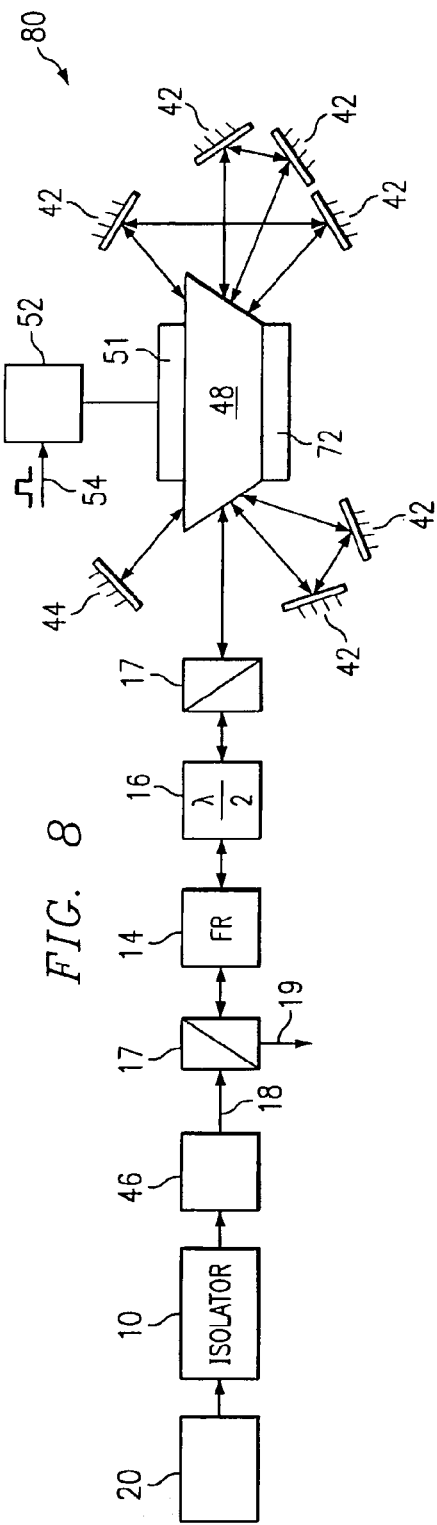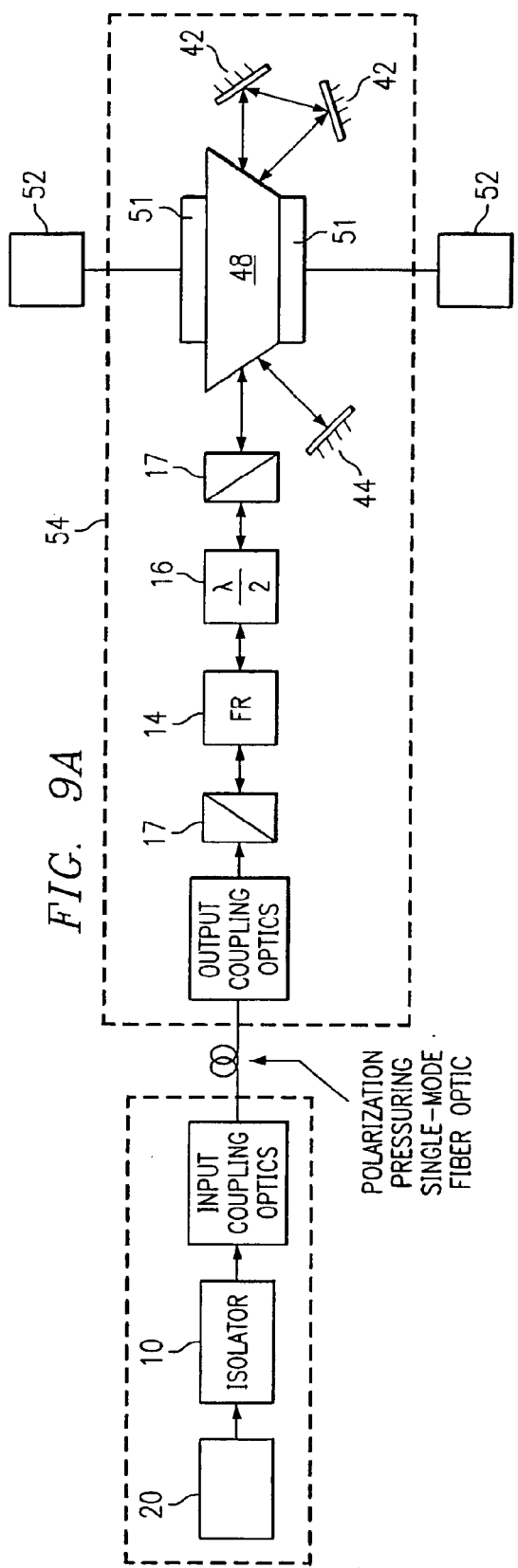

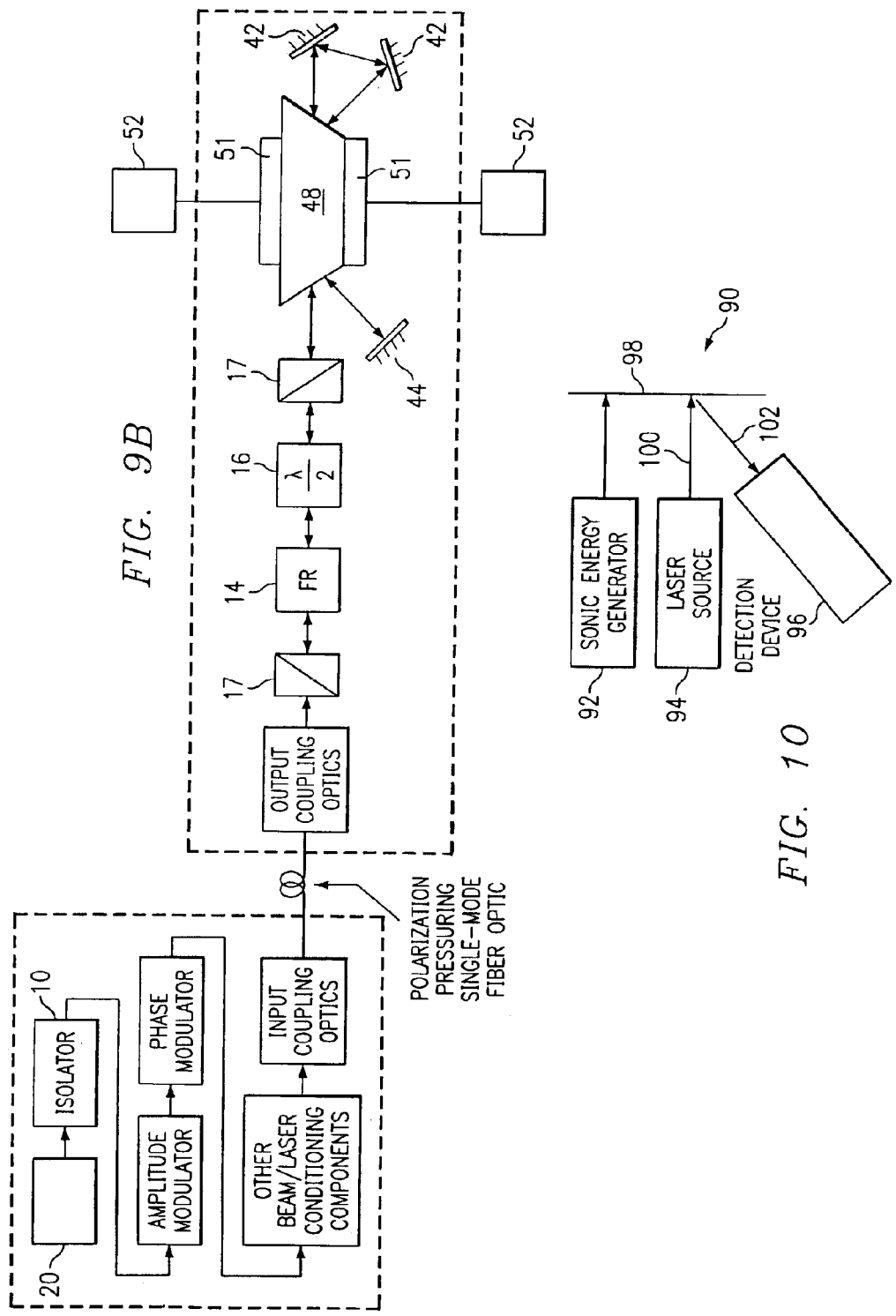

SYSTEM AND METHOD FOR HIGH-SPEED LASER DETECTION OF ULTRASOUND

This application is a continuation-in-part of U.S. patent application Ser. No. 09/344,298, filed Jun. 2, 1999 now U.S. Pat. No. 6,483,859, entitled: "System and Method for High-Speed Laser Detection of Ultrasound", and is incorporated herein by reference in its entirety.

TECHNICAL FIELD OF THE INVENTION

The present invention relates generally to a system and method for laser light amplification and, more particularly, to a system and method for providing amplification of a laser beam emitted from a solid state laser that provides higher pulse rates, improved pointing stability, and optionally variable pulse rates for a variety of uses, including for non-destructive laser ultrasonic testing of materials.

BACKGROUND OF THE INVENTION

Amplification of laser light is required for a variety of applications. Long haul telecommunication applications, such as those employing single mode optical fiber, often require optical repeater/amplifiers to boost sagging signal levels. Material processing applications may require very high power laser light to perform functions such as cutting of various materials and preparation of material surfaces. Applications requiring intense energy pulses of laser light employ some configuration for providing either time-varying optical amplification or intensity modulation of laser light.

One method for amplifying a laser beam is to employ a laser medium whose optical gain may be controlled by optical pumping. Optical pumping of a solid state laser medium is a common and conventional method used to create a population inversion of energy states for laser applications requiring high-gain. The laser medium providing high-gain, when optically pumped, may comprise a material such as neodymium yttrium-aluminum garnet ($Nd^{3+}$:YAG), neodymium glass ($Nd^{3+}$:glass), Erbium doped optical fiber ($Er^{3+}$:silica), or Ruby rods ($Cr^{3+}$:$Al_2O_3$). These materials are merely exemplary candidates for high-gain laser media, and those skilled in the art will appreciate that any suitable material capable of maintaining an inverted population of energy states when optically-pumped may serve as an optical amplifier. Those laser media utilizing $Nd^{3+}$:YAG are common, given the substantial optical gain near desired wavelengths near the 1.064:m range. Additionally, $Nd^{3+}$:YAG laser media provide linearity of pumping rate with respect to inverted population given its four-level transition system.

To saturate an entire laser medium with an inverted population through optical pumping, a conventional method is to distribute a large array of laser diodes across the surface of the laser medium to form a pumping array. The light emitted from the individual laser diodes of the pumping array excites the laser medium and provide a very high optical gain for the energy transition level of the optically-pumped, inverted population within the high-gain laser medium, e.g., near the 1.064:m range for $Nd^{3+}$:YAG, near the 1.06:m range for $Nd^{3+}$:glass, near the 0.6943:m range for $Cr^{3+}$:$Al_2O_3$, near the 1.55:m range for $Er^{3+}$:silica, etc.

An integrated approach to performing laser light amplification and generating optical pulses utilizes gain switching of a laser medium. In this method of providing a high energy pulsed laser beam, the optical pumping of a high-gain laser medium itself is pulsed to generate a time varying gain of the high-gain laser medium through which a laser beam is propagating. This results in a pulsed output laser beam after an original laser light source has traveled through the high-gain laser medium that is being optically pumped in a time varying manner.

Each optical pumping cycle takes the high-gain laser medium through a transition which consists essentially of generating a sufficient energy state population through optical pumping to reach threshold for amplification. Before the optical pumping begins, the population of energy states is initially below threshold and optical amplification does not occur. After the high-gain laser medium has operated in an amplification mode for some time, then optical pumping is switched off, and the energy state population is subsequently depleted. By turning off the optical pumping, the population falls below threshold and the optical amplification is interrupted until the optical pumping again resumes and the population of energy states again reaches threshold. Such a method provides for a pulsing of the conditions in which laser light amplification may occur. Such a method is preferable to a method which merely blocks a highly amplified laser beam in that design considerations need not include the potentially loss energy due to the dumping of electromagnetic energy into a shutter assembly. Many other advantages are inherent to the fact that the solution is electronic, not incorporating any mechanical components for a mechanical shutter system.

Another method for providing an electronic solution is to generate a high energy pulsed laser beam to maintain continuous optical pumping of the high-gain laser medium and to modulate the high-gain laser medium's loss coefficient. One method to perform such loss switching is to electronically modulate an optical absorber that is placed within the optical resonator cavity next to the high-gain laser medium. Such a configuration will permit the user to control the loss of the laser light traveling through the high-gain laser medium as opposed to controlling the rate at which optical pumping occurs. Those skilled in the art will recognize a variety of methods for performing loss switching of laser light contained within a the high-gain laser medium including electrical modulation of an electro-optic crystal to perform intensity modulation of the laser beam.

Such a method is an extension of the gain switching method as an optical resonator's threshold energy state population difference is proportional to the resonator's loss coefficient. In this method, the loss coefficient is modulated to provide intermittent periods when the optical loss of the high-gain laser medium is prohibitively high to maintain oscillation. This results is creating an increased energy state threshold population to sustain oscillation, given the increased loss of the high-gain laser medium. Even though the energy state population would be sufficiently high for oscillation were the loss coefficient of the high-gain laser medium not increased, no optical amplification can occur during the period when the loss coefficient is elevated.

When the loss is suddenly decreased during the transition of a pulsing cycle of the loss coefficient, the energy state population begins to deplete resulting from the decreased optical losses. The high-gain laser medium will amplify the laser light during the period when the energy state population exceeds the threshold condition for oscillation during the period that the loss coefficient is minimum. However, as the population continues to decrease, the population will eventually fall below the newly established energy state threshold for oscillation corresponding to the period of time when the loss coefficient is at its minimum during a modulation cycle.

These methods of performing electronic switching of either the gain or loss coefficients of the high-gain laser medium often employ flashlamp optical pumping. The use of such a light source for performing the optical pumping presents some undesirable effects which significantly limit performance of the high-gain laser medium in providing pulses of laser light including the maximum pulse rate of the laser beam and the intensity with which the optical pumping must be performed. Such inherent problems may present significant problems for applications which require high pulse rates and suffer from limited power budgets.

Another problem that is introduced by the utilization of flashlamps to provide optical pumping is the broad spectral width of flashlamp produced light may prove very inefficient in that a large proportion of the light produced by the flashlamp does not serve to generate the inverted population of energy states. Flashlamp light outside of the spectral density range required for generating the inverted population is simply lost into the high-gain laser medium in the form of thermal heating. This heating of the high-gain laser medium may itself produce undesirable effects including beam pointing errors and self-focusing. The heating of the high-gain laser medium may increase to such levels that fracture of the solid-state crystals will limit the maximum peak or average power.

The pulse rate at which the laser amplifier may be switched is also limited by the physical properties of the flashlamps which provide the optical pumping. The electrical switching of the flashlamps is often associated with the thermal heating problems associated with the flashlamps themselves. This upper limit of pulse rate may also be determined in part by the intensity level at which the flashlamps must operate to generate an inverted energy state population above threshold. For example, if the energy transition of interest is near the periphery of the spectral density of the flashlamp, the flashlamp may necessitate operation at a very high power level to generate the inverted population. Such a situation may at the very least limit the duty cycle of the pulse rate to avoid overheating of the flashlamps themselves.

Additionally, the flashlamps intrinsically possess a start up time constant before they begin optical pumping. They do not respond instantaneously with the vertical transition of the electric signal which drives them. Consequently, the maximum pulse rate of the optical amplifier may be limited by the time constant corresponding to the start up of the flashlamps. Another consequence of the intrinsic response limitations of the flashlamps is a lower limit on the width of the pulse which may be generated using such a laser amplification system. Such a problem stems from the similar characteristic of the flashlamps in that they are limited in the speed with which they may switch on and off. The minimum pulse width which may be generated is often dictated by the minimum time in which the flashlamps may turn on and then turn off, including considering of the start up time constant of the flashlamps and evanescent decay of radiation from the flashlamps when turned off.

The present invention overcomes or eliminates the problems and limitations of known systems and methods for detecting high-speed laser-induced ultrasound to provide a system and method for laser beam amplification from a solid state laser that yields high pulse rates, improved pointing stability, and optionally variable pulse rates for non-destructive laser ultrasonic testing of materials, as well as a variety of other uses.

SUMMARY OF THE INVENTION

According to one aspect of the present invention, there is provided a method for generating an amplified laser beam at a high pulse rate that includes generating a low-amplification seed laser light signal. The method further includes transmitting the low-amplification seed laser light signal to an amplification component. The low-amplification seed laser light signal is amplified in the amplification component by stimulating emissions of the population inversion that a pumping diode provides. The result of this amplifying step is to yield an amplified laser light signal. The amplified laser light signal is then directed to an output destination. The light signal may scatter from the output destination and be collected in an interferometer.

The present invention provides a system and method for providing amplification of laser light from a solid state laser while maintaining the physical properties of the laser light by minimizing amplification induced distortion. A seed laser possessing desired physical properties including a single longitudinal mode with a desired linewidth is passed through a high-gain laser medium. The high-gain laser medium may take the form of a diode pumped rod or slab, among others. The high-gain laser medium is optically pumped using a pumping array of laser diodes distributed across the high-gain laser medium. The electric current which drives the pumping array may be a time-varying signal which consequently provides time-varying optical gain and lasing conditions within the laser medium. The amplified laser beam may then be pulsed at a pulse rate corresponding to the frequency of the time-varying signal comprising the electric current which drives the pumping array of laser diodes.

The present invention may be employed in applications which require a particularly narrow or pure spectral density such as applications involving optical interferometry which often require a single longitudinal mode having a very stable center frequency and linewidth. For such applications in which the purity of the initial seed laser is amplified to generate a pulse stream of laser light having a desired intensity level, duty cycle and pulse rate, an optical isolation assembly may be used to minimize back reflection of the laser light into the seed laser light source. Undesirable parasitic feedback may corrupt the seed laser source resulting in deleterious performance of the seed laser including amplitude noise and multimode operation. Such effects may be disastrous for those applications requiring a spectrally pure laser source. One method, for providing optical isolation of a laser beam which minimizes back reflections into the original light source comprises a Faraday rotator and two polarizers which provide for light propagation in only one direction through the optical isolation assembly by using the non-reciprocal rotation of a polarized lightwave provided by a Faraday rotator.

Additional optical isolation assemblies may be included in the invention for providing beam splitting of the original laser beam for directing the amplified, pulsed output laser beam or directing of the original laser beam through the high-gain laser medium multiple times for even greater amplification than a single pass through the high-gain laser medium.

The present invention generates an amplified and pulsed laser beam which possesses similar physical properties of the original seed laser including a desired center frequency and linewidth for use within an optical interferometer to perform ultrasonic detection. Additionally, the output intensity of the pulsed, amplified laser beam may be modulated to extend the dynamic range of detection within an optical interferometric system. Electro-optic modulators comprising Pockels or Kerr effect crystals provide intensity modulation of a laser beam.

The present invention may perform optical pumping of a high-gain laser medium using a pumping array of laser diodes. This method permits optical pumping within a very narrow wavelength regime selected by the use of appropriate laser diodes to minimize optically-induced thermal heating of the laser medium. This advantage is provided primarily by the fact that the appropriate choice of laser diodes which comprise the pumping array may be chosen to optically pump within a specific wavelength regime thereby not incurring significant thermal heating by radiation bombardment of the high-gain laser medium with optical pumping outside of the energy transition level of interest.

The present invention may provide for maximizing the pulse rate and controlling the pulse width of the resulting amplified pulsed laser beam by performing the optical pumping using a pumping array comprising a multiplicity of laser diodes. The maximum pulse rate for the present invention will be determined largely by the speed at which the laser diodes may be turned on and turned off and the allowed duty cycle.

The present invention may minimize amplification induced distortion of a seed laser beam. Many applications, including optical interferometry, require a highly amplified beam with a uniform wavefront and good pointing stability.

The present invention may provide for intensity modulation of the output laser beam thereby expanding the detection dynamic range within interferometric systems.

As such, a system for generating a laser for use with an interferometer is described. Other aspects, advantages and novel features of the present invention will become apparent from the detailed description of the invention when considered in conjunction with the accompanying drawings.

BRIEF DESCRIPTION OF THE DRAWINGS

For a more complete understanding of the present invention and the advantages thereof, reference is now made to the following description taken in conjunction with the accompanying drawings in which like reference numerals indicate like features and wherein:

FIG. 8 shows another possible embodiment of the invention comprising an eight pass, single slab laser medium pulsed laser light source;

FIG. 9A shows one alternative embodiment of the present invention; and

FIG. 9B shows still a further alternative embodiment of the present invention.

FIG. 10 shows a schematic block diagram of an exemplary embodiment of the present invention.

DETAILED DESCRIPTION OF THE INVENTION

Embodiments of the present invention are illustrated in the FIGUREs, like numerals being used to refer to like and corresponding parts of the various drawings.

The present invention provides a system and method for providing amplification of laser light from a solid state laser while maintaining the physical properties of the laser light while minimizing amplification induced distortion. A seed laser possessing desired physical properties including a single longitudinal mode with a desired linewidth is passed through a high-gain laser medium. The center frequency of the seed laser source may be chosen appropriately as to perform within specific applications such as optical interferometry which require very coherent light. The high-gain laser medium may be, for example, optically pumped using a pumping array of laser diodes distributed across the high-gain laser medium. The electric current which drives the pumping array may be a time-varying signal which consequently provides time-varying optical gain and lasing conditions within the laser medium. The amplified laser beam may then be pulsed at a pulse rate corresponding to the frequency of the time-varying signal comprising the electric current which drives the pumping array of laser diodes.

Figure 1A:
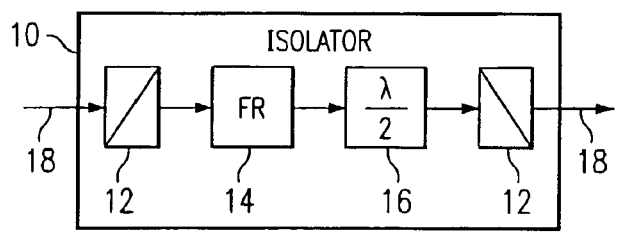
FIG. 1A shows a polarization selective assembly comprising an optical isolator.

FIG. 1A shows a polarization selective assembly comprising an optical isolator 10. A typical arrangement of an optical isolator passes a laser beam 18 through a first polarizer 12. The polarized light then passes through a Faraday rotator 14. A Faraday rotator provides optical rotation of a polarized light way in a non-reciprocal fashion. That is to say, polarized light passes through the Faraday rotator will rotate in one and only one direction regardless of the direction of propagation of the laser beam through the material. For example, a laser beam 18 traveling through Faraday rotator 14 rotates clockwise as it propagates in the direction of the arrows of laser beam 18, then a laser beam 18 traveling in the opposite direction of the arrows of laser beam 18 will also rotate clockwise. Faraday rotators 14 are well known to those skilled in the art, and may comprise a number of materials including yttrium-iron-garnet (YIG) or terbium-gallium-garnet (TGG).

The first polarizer 12 transmits only P-state light from the input 18. After traveling through Faraday rotator 14, laser beam 18 is rotated 45°. Following the Faraday rotator is a half waveplate 16 which provides an additional 45° of polarization rotation in the opposite direction of Faraday rotator 14. Light polarized in a P-state traveling in the direction of the arrows has a net rotation of zero. A half waveplate and its operation are well known to those skilled in the art. Light polarized in a p-state traveling in the direction of the arrows of laser beam 18 through the optical isolator 10 travels unencumbered, yet light (possibly unpolarized, such as from random scattering) traveling in the opposite direction of the arrows of laser beam 18 through the optical isolator 10 is blocked. This stems from the fact that the Faraday rotator exhibits non-reciprocal angular rotation of a polarized light beam. Light traveling in the opposite direction of the arrows of laser beam 18 is polarized by the a polarizer 12, then pass through a half waveplate 16 and then through the Faraday rotator 14 for a net rotation of 90°. The Faraday rotator 14 will rotate the light one half of the angular difference between the two polarizers 12 so that when light traveling in the opposite direction of the arrows of laser beam 18 meets the originally first polarizer 12, at an angle of incidence that is perpendicular to the polarizer's pass axis thereby completely blocking back reflections through the optical isolator 10. In effect, an optical isolator 10 serves as an optical diode or check valve.

Figure 1B:
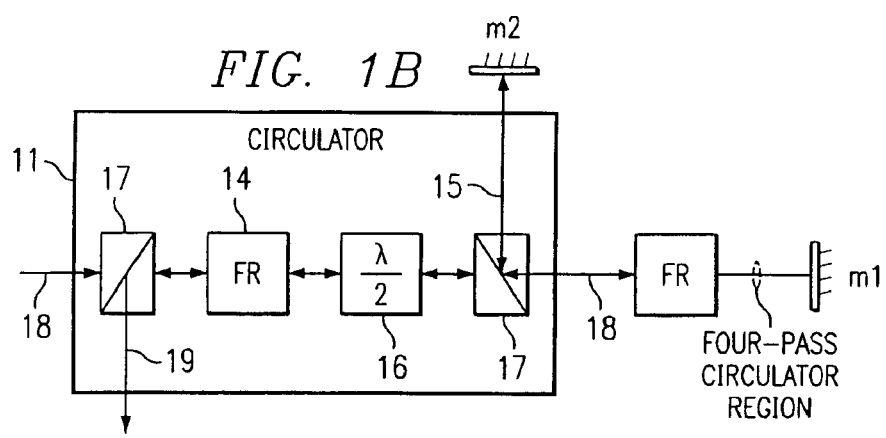
FIG. 1B shows a polarization selective assembly comprising a four port optical device providing polarization selective directing of a laser beam.

FIG. 1B shows a polarization selective circulator assembly comprising a four port optical device 11 providing polarization selective directing of a laser beam. A laser beam 18 enters a polarizing beam splitter 17 in which polarized light aligned to one axis of the polarizing beam splitter 17 passes through, and polarized light not aligned to that one axis of the polarizing beam splitter 17 is rejected. For the portion of laser beam 18 which passes through polarizing beam splitter 17, it then passes through a Faraday rotator 14 followed by a half waveplate 16 for directing the laser beam 18. Another polarizing beam splitter 17 may be used to direct the remaining portion of laser beam 18 again into two sub-components comprising gain path laser beam 13 and aperture path laser beam 15. Four port optical device 11 may be used to provide steering of components of laser beam 18 in various directions within an optical circuit while minimizing back reflections in the opposite direction of the arrows of laser beam 18.

Figure 2:
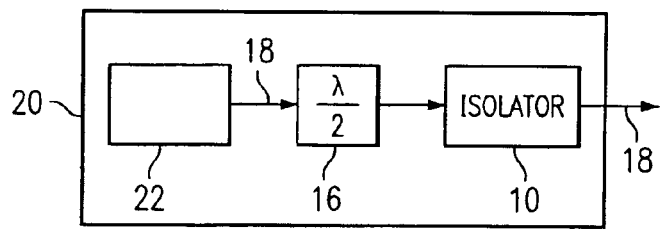
FIG. 2 shows a configuration of a laser light source capable of preventing optical feedback and varying the intensity variation of the laser light by rotating a half waveplate.

FIG. 2 shows a first configuration of a laser light source 20 capable of preventing optical feedback and varying the intensity variation of the laser light by rotating a half waveplate. Laser light source 22 may comprise a single longitudinal light source operated at continuous wave operation. The emitted laser beam 18 from the laser light source 22 inherently possesses a significant polarization and a half waveplate 16 permits the aligning of that polarization along a predetermined axis of polarizer 12 contained within optical isolator 10. Such a configuration is used to minimize any parasitic, undesirable back reflection of laser light into the laser light source 22 which may result in deleterious effects such as wavelength drift and linewidth broadening of the laser light source 22. The half waveplate 16 may be angularly aligned to various angles of incidence of the polarizer 12 to vary the intensity of the laser beam 18 which exits laser light source 22 and travels through the optical system. Those skilled in the art will recognize that a number of optical isolators 10 may be used to decrease even further the possibility of back reflected light into the laser light source 22 by cascading several optical isolators 10.

Figure 3:
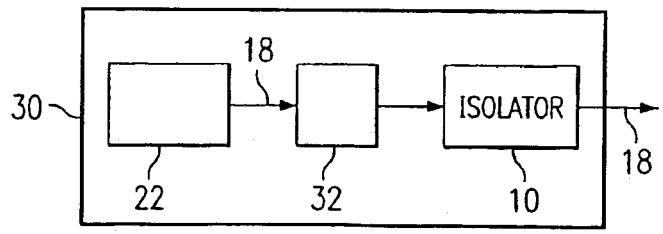
FIG. 3 shows another configuration of a laser light source capable of preventing optical feedback and varying the intensity variation of the laser light using an electro-optic modulator.

FIG. 3 shows another configuration of a laser light source 30 capable of preventing optical feedback and varying the intensity variation of the laser light using an electro-optic modulator. An optical isolator 10 may also be used to prevent reflected light from entering into the laser light source 22 and causing undesired effects as described above. Additionally, an intensity modulator 32 may be placed either in front of the optical isolator 10 or after for modulating the intensity of the laser beam 18 as it then travels through the remainder of an optical circuit. Those skilled in the art will recognize a wide variety of electro-optic modulators which will serve the function of intensity modulator 32 including Pockels effect elements utilizing the linear electro-optic effect and Kerr effect elements utilizing the quadratic electro-optic effect. A very common material candidate for a Pockels cells is Lithium niobate ($LiNbO_3$).

Figures 4, 5:
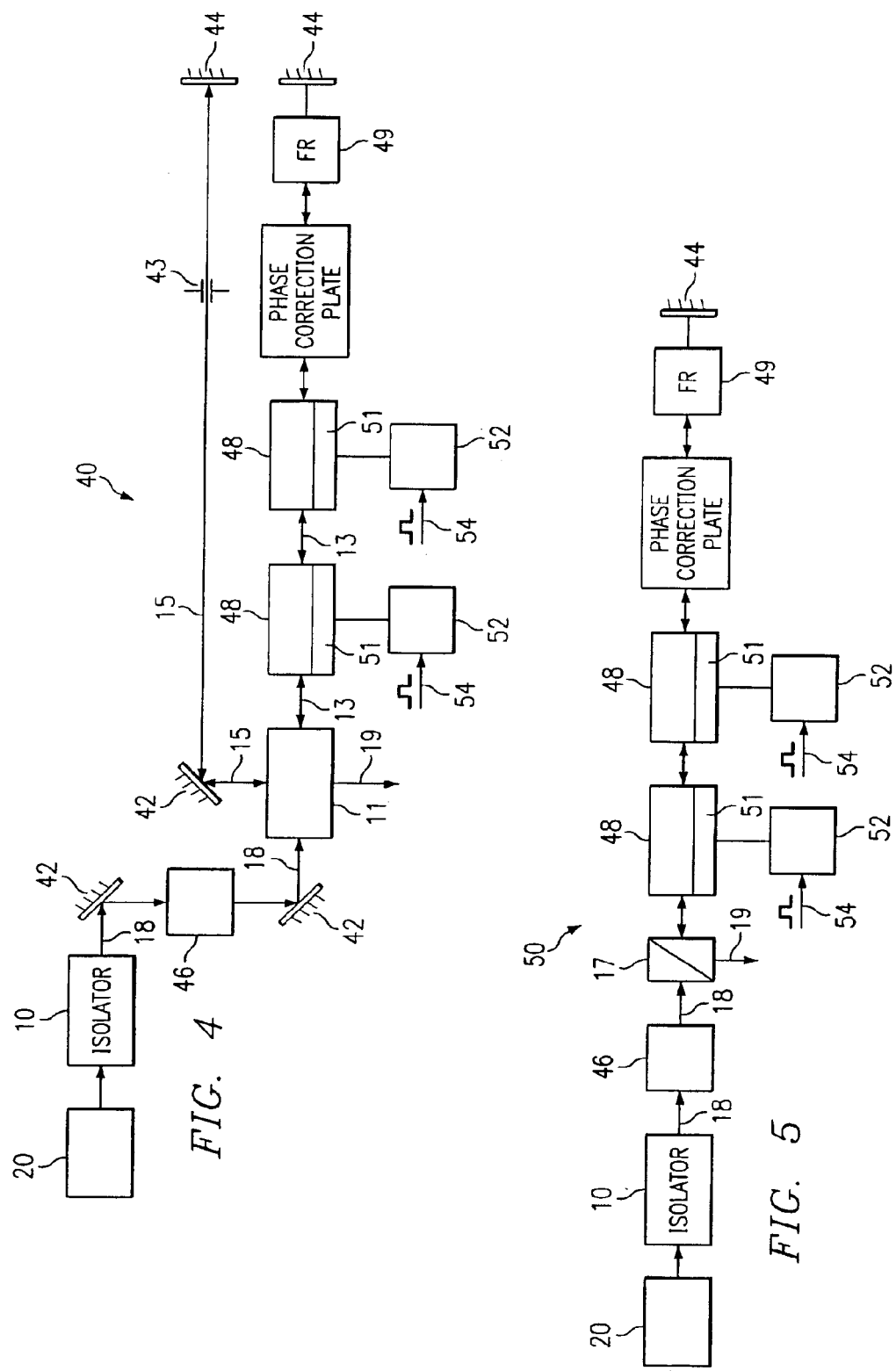
FIG. 4 shows one possible embodiment of the invention comprising a four pass, dual rod laser media pulsed laser light source.
FIG. 5 shows another possible embodiment of the invention comprising a dual pass, dual rod laser media pulsed laser light source.

FIG. 4 shows one possible embodiment of the invention comprising a four pass, dual [could be a single or "n" rods; two is just an example] rod laser media pulsed laser light source 40. Note, however, that source 40 may be formed of one or many rods or slabs, as other considerations may dictate. This embodiment shows laser light source 20 which emits laser beam 18 which passes through an isolator 10 and is directed using a first mirror 42 through a beam expander 46 for broadening the beam waist of laser beam 18 to minimize the divergence of laser beam 18 as it propagates through free space given its inherently Gaussian nature. Laser beam 18 then passes through four port optical device 11 in which laser beam 18 is directed to the gain path laser beam 13. The gain path laser beam 13 passes through two high-gain laser media 48 and then through a phase correction plate and a Faraday rotator 49 where the linear polarization of laser beam 18 is rotated 45°.

Typically, high-gain laser media 48 comprising glass materials such as $Nd^{3+}$:glass are inherently amorphous and non-birefringent whereas semiconductor materials such as $Nd^{3+}$:YAG might degrade the polarization state of laser beam 18 as it passes through them. In the case of optically birefringent high-gain laser media, the use of an adjustable waveplate for phase compensation can improve the performance of the system. The phase correction plate compensates for any rod birefringence, which may be thermally induced. The high-gain laser media 48 may comprise any material that will sustain an inverted population of energy states when optically pumped. It then reflects off of an end mirror 44 which then passes through the Faraday rotator 49 again where it is rotated an additional 45°, orthogonal to the polarization of the original laser beam 18.

The reflected laser beam then passes a second time through high-gain laser media 48 and into four port optical device 11 where it is directed into the direction of aperture path laser beam 15 and then reflects off a mirror 42 where it passes through an aperture 43 which helps to minimize self-oscillations caused by amplified spontaneous emissions from the gain medium. Beam 15 reflects at end mirror 44 retracing its path back into four port optical device 11 where it is again directed to pass through high-gain laser media 48 for a third pass. It then travels through to Faraday rotator 49 and to end mirror 44 where it is again reflected and retraces its path in passing through Faraday rotator 49, being converted into the same linear polarization as the original gain path laser beam 13 in its first pass through high-gain laser media 48. The gain path laser beam 13 then passes a fourth time through high-gain laser media 48 and into the four port optical device 11 where it is directed to pass out in the direction of output laser beam 19.

Each high-gain optical medium 48 is optically pumped to generate an inverted population of energy states using a pumping array 51 of laser diodes driven by a diode driver 52 which delivers electric current to operate the laser diodes of the pumping array 51. To generate pulses of amplified laser light, a trigger signal 54 is used to drive the diode driver 52 which operates the pumping array 51 of laser diodes. The pulse rate at which the output laser beam 19 may be pulsed is governed most directly by the frequency of the trigger signal 54 which is used to pulse the diode driver 52. The switching of the optical pumping results in gain switching of the high-gain laser medium 48 which serves to provide for a pulsing of the conditions in which laser light amplification may occur. The result is an amplified, pulsed output laser beam 19.

FIG. 5 shows another possible embodiment of the invention comprising, for example, a dual pass, dual rod laser media pulsed laser light source 50. This embodiment is strikingly similar to four pass, dual rod laser media pulsed laser light source 40. The main difference is that there exists no four port optical device 11 is replaced by a single polarizing beam splitter 17.

Figure 6:
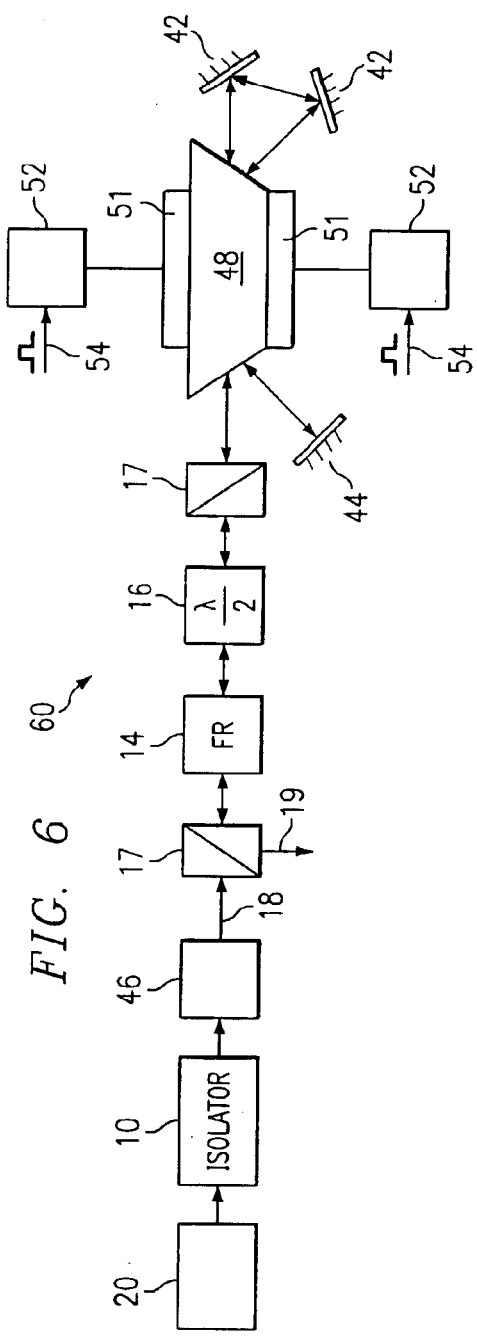
FIG. 6 shows another possible embodiment of the invention comprising a four pass, single slab laser medium pulsed laser light source.

FIG. 6 shows another possible embodiment of the invention comprising, for example, a four pass, single slab laser medium pulsed laser light source 60. This embodiment shows laser light source 20 which emits laser beam 18 which is isolated from feedback with isolator 10 and is directed through beam expander 46 for broadening the beam waist of laser beam 18 to minimize the divergence of laser beam 18 as it propagates through free space given its inherently Gaussian nature. Laser beam 18 then passes through polarizing beam splitter 17 in which polarized light aligned to one axis of the polarizing beam splitter 17 passes through, and polarized light not aligned to that one axis of the polarizing beam splitter 17 is redirected in the direction of an output laser beam 19. For the portion of laser beam 18 which passes through polarizing beam splitter 17, it then passes through a Faraday rotator 14 followed by a half waveplate 16 and a second polarizer 17 for directing the laser beam 18 through high-gain laser media 48. Slab designs pass P-state with high efficiency because the face is almost at Brewsters Angle. The high-gain laser media 48 may comprise any material that will sustain an inverted population of energy states when optically pumped. It then reflects off of turning mirror 42. The reflected laser beam then reflects off of a second turning mirror 42, passes a second time through high-gain laser media 48 and is directed into the direction of laser beam 15 and then reflects off end mirror 44 before retracing its path back into the high-gain laser media 48 for a third pass. It then reflects off mirror 44 to mirror 44 where it is again reflected and retraces its path in passing through high-gain laser media 48 for a fourth time and into the polarizer 17 and half waveplate for aligning the laser beam along a predetermined incidence angle. The laser beam 18 then passes a second time through Farady rotator 14. After traveling through Faraday rotator 14, the laser beam 18 has been rotated to be orthogonal to the original laser beam. Laser beam 18 enters polarizing beam splitter 17 where it is directed to pass out in the direction of output laser beam 19.

In the present example, each high-gain optical medium 48 is optically pumped to generate an inverted population of energy states using pumping arrays 51 of laser diodes driven by a diode driver 52 which delivers electric current to operate the laser diodes of the two pumping arrays 51. To generate pulses of amplified laser light, a trigger signal 54 is used to drive the diode driver 52 which operates the pumping arrays 51 of laser diodes. The pulse rate at which the output laser beam 19 may be pulsed is governed most directly by the frequency of the trigger signal 54 which is used to pulse the diode driver 52. The switching of the optical pumping results in gain switching of the high-gain laser medium 48 which serves to provide for a pulsing of the conditions in which laser light amplification may occur. The result is an amplified, pulsed output laser beam 19.

Figure 7:
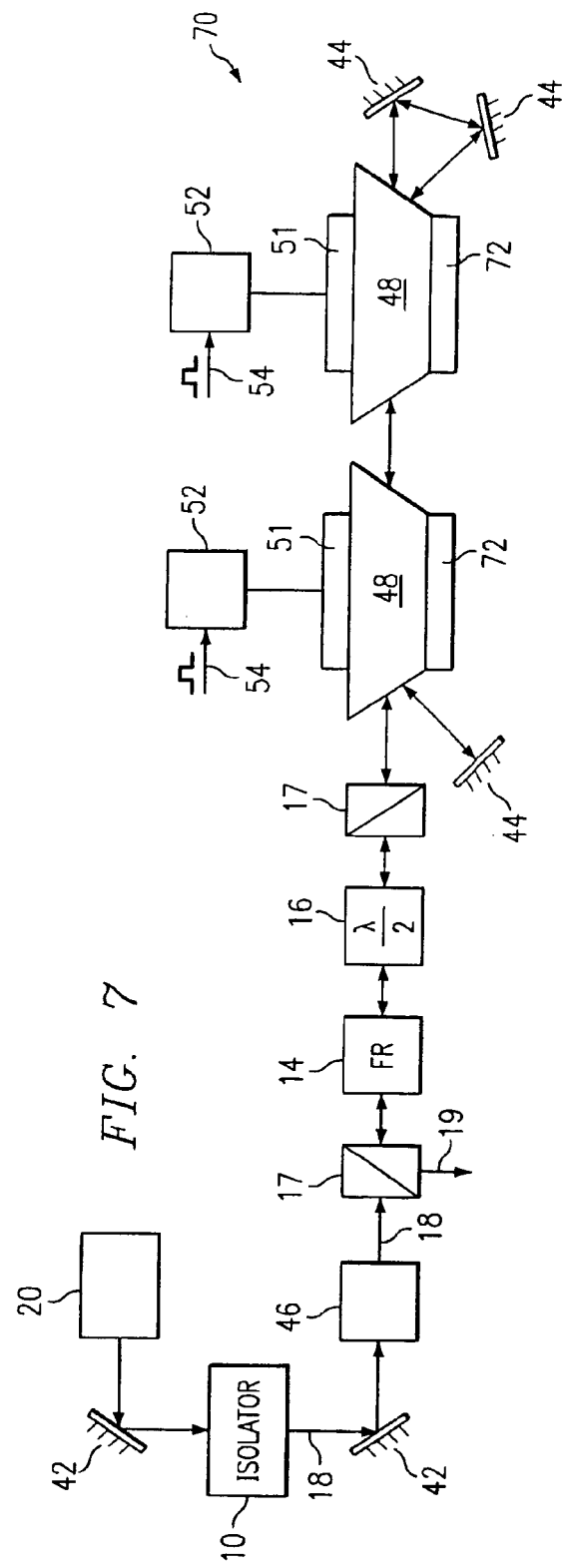
FIG. 7 shows another possible embodiment of the invention comprising a four pass, dual slab laser media pulsed laser light source.

FIG. 7 shows another possible embodiment of the invention comprising a four pass, dual slab laser medium pulsed laser light source 70. This embodiment is strikingly similar to four pass, single slab laser medium pulsed laser light source 60, in that it uses the same number of diodes as in the FIG. 6 example. The main difference is that there exists a second slab laser medium 48 and mirror assemblies 72 (either mirrors or coatings) are placed on both of the high-gain laser media 48. This may result in a system that is more efficient (per diode) than the system of FIG. 6, but with only a small added cost of the second slab.

FIG. 8 shows another possible embodiment of the invention comprising an eight pass, single slab laser medium pulsed laser light source 80. This embodiment is strikingly similar to four pass, single slab laser medium pulsed laser light source 60. The main difference is that there exists a plurality of turning mirrors 42 to direct the laser beam through the high-gain laser media 48 eight times and mirror assembly 72 (either mirrors or coatings) is placed on the high-gain laser media 48.

FIG. 9A shows another possible embodiment of the present invention. FIG. 9A includes remote seeding of amplifier 54 with a fiber optic link. Laser light source 20 emits laser beam 18 which is isolated from feedback with optical isolator 10 and directed into input coupling optics and polarization preserving single-mode fiber optics. Polarization preserving single-mode fiber optic is coupled to amplifier 54, which includes output coupling optics. Amplifier 54 (not including output coupling optics) is equivalent to the amplifier section shown in FIG. 6. Amplifier methods illustrated in FIG. 4, 5, 7 or 8 can be used, as well. Long-term stability of amplifier 54 is improved by de-coupling of laser beam 18. If laser beam 18 laser "walks" but part of the light still couples into the polarization preserving single-mode fiber optic, then output of amplifier 54 may only drop a small amount.

FIG. 9B shows another possible embodiment of the present invention. FIG. 9B represents remote seeding of amplifier with internal modulators. Laser light source 20 emits laser beam 18 which is isolated from feedback with optical isolator 10. Laser beam 18 is input in amplitude modulator, phase modulator and other beam/laser conditioning components. Prior to being input to polarization preserving single-mode fiber optics, laser beam 18 is input to input coupling optics. Laser beam 18 is output from polarization preserving single-mode fiber optics to output coupling optics. Laser beam 18 is amplified in a manner similar to that shown in FIG. 6. Amplifying methods illustrated in FIG. 4, 5, 7 or 8 can be used, as well.

The present invention provides several benefits including minimizing thermal heating of the high-gain laser medium by using laser diodes to perform the optical pumping. Using laser diodes which operate within a very narrow wavelength regime minimize optically-induced thermal heating of the laser medium in that little electromagnetic radiation outside of the desired spectrum bombards the high-gain laser medium as with conventional methods.

Using laser diodes for optically pumping the high-gain laser medium provides additional benefits including permitting a faster pulse rate, variable pulse rate. By performing optical amplification and pulsing in the manner described above, the present invention also minimizes amplification induced distortion of a seed laser beam. Consequently, the physical properties of the original seed laser beam are maintained in the resultant amplified, output beam. Many applications including optical interferometry require a highly amplified, spectrally pure output laser beam which the present invention will provide. To broaden the dynamic detection range of an optical interferometer employing the present invention, the intensity of the output laser beam may also be modulated.

FIG. 10 shows an exemplary embodiment of the amplification system as used in an optical interferometry application. In this exemplary application, an ultrasound testing system 90 has a sonic energy generator 92, a laser source 94, and a detection device 96. However, the system may be envisioned in various configurations with some, all, or none of these items. For example, the system 90 may have a laser source 94 and a detection device 96.

The sonic energy generator 92 may take various forms. These forms may include a laser or a transducer, among others. The sonic energy generator may generator a sonic energy wave in the object 98. For example, a laser may direct a coherent beam of electromagnetic energy at the object 98. The electromagnetic energy may impart heat energy to the object causing a thermal expansion. As a result of the expansion, a sonic energy wave may by produced in the object 98. However, other means may be employed to produce a sonic energy wave such as transducers, or applied stress, among others.

The laser source 94 may take the forms as described above. Referring to FIGS. 1B, and 4–8, the beam 19 may be directed at an object. Returning to FIG. 10, the beam may be directed at an object 98. The beam may be modulated by the sonic energy wave propagating about the object 98. Further, the beam may reflect from the object to become a modulated reflected beam 102.

The modulated reflected beam 102 may be collected in a detection device 96. The detection device may, for example, be an interferometer. The interferometer may take many forms. These forms may include a Fabry-Perot interferometer, a two-wave mixing interferometer, and a dual differential confocal Fabry-Perot interferometer, among others. However, various alternate detection devices may be envisaged including a gas-coupled laser acoustic detector and others.

Although the present invention has been described in detail, it should be understood that various changes, substitutions and alterations can be made hereto without departing from the spirit and scope of the invention as described by the appended claims.

What is claimed is:

1. A system for measuring sonic energy in a test object, the system comprising:
   a sonic energy generator, the sonic energy generator operable to generate the sonic energy about the test object;
   a source of coherent electromagnetic energy, the source of coherent electromagnetic energy directing at least one pulse of electromagnetic energy at the test object, the source of coherent electromagnetic energy further comprising:
      a low amplification seed laser light source; and
      an amplification component, the low amplification seed laser light source transmitting at least one low amplification seed laser light signal to the amplification component, the amplification component further comprising:
         at least one amplification medium with time varying optical gain driven by a time varying signal, the low amplification seed laser light signal traversing the at least one amplification medium; and
         at least one pumping diode, the at least one amplification medium amplifying the low amplification laser light signal by stimulating emissions of a population inversion provided by the at least one pumping diode to generate an amplified laser light signal, wherein the amplified laser light signal varies with the time varying optical gain; and
   an interferometer, the interferometer collecting at least one scattered light signal produced by a scattering from the object of the at least one pulse of electromagnetic energy with sonic energy in the test object, wherein the interferometer outputs a signal representative of the sonic energy in the test object; and
   a processor operable to process the output of the interferometer to obtain information about an internal structure of the test object.

2. The system of claim 1 wherein the low amplification seed laser light signal is amplified by repeatedly traversing the at least one amplification medium.

3. The system of claim 1, the system further comprising:
   a generation laser beam applied to the test object coaxially with the at least one pulse of electromagnetic energy.

4. The system of claim 1, wherein the source of coherent electromagnetic energy further comprises:
   an isolator associated with the low amplification seed laser light source, the isolator isolating the low-amplification seed laser light source from the amplification component.

5. The system of claim 1 wherein the at least one amplification medium is a diode pump rod.

6. The system of claim 1 wherein the at least on e amplification medium is a diode pump slab.

7. A method for measuring a sonic energy signal about a test object, the method comprising:
   generating sonic energy about the test object;
   generating a low amplification seed laser light signal from a low-amplification seed laser light source;
   transmitting said low-amplification seed laser light signal to an amplification component, wherein the amplification component has a time varying optical gain driven by a time varying signal;
   amplifying said low-amplification seed laser light signal in said amplification component by stimulating emissions of the population inversion provided by a pumping diode to generate an amplified laser light signal, wherein the amplified laser light signal varies with the time varying optical gain;
   directing said amplified laser light signal to test object;
   collecting a scattered light signal associated with said amplified laser light signal in an interferometer; and
   processing an output of the interferometer to obtain information about an internal structure of the test object.

8. The method of claim 7, wherein said amplifying step further comprises repeatedly directing said low-amplification seed laser light signal through said amplification medium.

9. The method of claim 7, wherein said directing step further comprises the step of extracting said low-amplification seed laser light signal from an isolator associated with said amplifier.

10. The method of claim 7, further comprising the step of isolating said amplification component from the source of said low-amplification seed laser light signal.

11. The method of claim 7, wherein said amplification component comprises a diode pump rod.

12. The method of claim 7, wherein said amplification component comprises a diode pump slab.

13. The method of claim 7, wherein said generating step further comprises the step of generating a continuous wave low-amplification seed laser light signal, and further wherein said amplifying step further comprises the step of amplifying said continuous wave low-amplification seed laser light signal to generate said amplified laser light signal having a maximum gain of a predetermined gain coefficient times the amplification of said continuous wave low-amplification seed laser light signal.

14. The method of claim 7, further comprising the step of isolating said low-amplification seed laser light source from said amplification component for preventing feedback into said low-amplification seed laser light source.

15. The method of claim 7, further comprising the step of isolating said amplification component from said output destination for extracting said amplified laser light signal from said amplification source.

16. The method of claim 7, further comprising the steps of:
transmitting said low-amplification seed laser light via an optical fiber to an isolator that interfaces with said amplification component; and
transmitting said amplified laser light signal through an optical fiber from said amplification component to said output destination.

17. The method of claim 7, wherein said generating step further comprises the step of generating microsecond pulses of said low-amplification seed laser light signal.

18. The method of claim 7, wherein said generating step further comprises the step of generating variable pulse rate pulses of said low-amplification seed laser light signal.

19. A system for measuring a sonic energy signal associated with a test object, the system comprising:
a sonic energy generator, the sonic energy generator operable to generate the sonic energy about the test object;
a seed laser light source for providing a leaser beam with a desired linewidth;
at least one optical isolation assembly placed in the path of propagation of the laser beam for preventing reflected laser light feedback into the seed laser light source;
a polarization selective assembly aligned in the path of propagation of the laser beam for directing a first polarization state of the laser beam in a first propagation direction and at least one additional polarization state of the laser beam in at least one additional propagation direction;
at least one pumping array comprising a multiplicity of laser diodes distributed across at least one high-gain laser medium having a time varying optical gain driven by a time varying signal, wherein the at least one high-gain laser medium aligned in the path of propagation of either the first polarization state or the at least one additional polarization state of the laser beam for optically pumping the at least one high-gain laser medium for generationg a population inversion of energy states within the at least one high-gain laser medium for amplifying the laser beam and generating an output pulse of laser light that varies with the time varying optical gain; and
an interferometer, the interferometer collecting scattered laser light associated with the output pulse of laser light, wherein the sonic energy in the test object scatters the output pulse of laser light and wherein the interferometer ouputs a signal representative of the sonic energy in the test object; and
a processor operable to process the output of the interferometer to obtain information about an internal structure of the test object.

20. The system of claim 19, further comprising:
a diode driver for delivering an electric current to the multiplicity of laser diodes for optically pumping the at least one high-gain laser medium; and
a trigger signal for pulsing the optical pumping of the high-gain laser medium by delivering the trigger signal to the diode driver for switching the electric current delivered to the at least one pumping array.

* * * * *